(12) United States Patent
Jabbarzadeh et al.

(10) Patent No.: US 11,439,655 B2
(45) Date of Patent: Sep. 13, 2022

(54) COMPOUNDS FOR USE IN WOUND HEALING AND ANGIOGENESIS

(71) Applicant: UNIVERSITY OF SOUTH CAROLINA, Columbia, SC (US)

(72) Inventors: Ehsan Jabbarzadeh, Columbia, SC (US); Sara Eslambolchi Moghadam, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/122,087

(22) Filed: Sep. 5, 2018

(65) Prior Publication Data

US 2019/0070205 A1    Mar. 7, 2019

Related U.S. Application Data

(60) Provisional application No. 62/645,829, filed on Mar. 21, 2018, provisional application No. 62/554,640, filed on Sep. 6, 2017.

(51) Int. Cl.
| | |
|---|---|
| *A61K 31/7048* | (2006.01) |
| *A61K 36/185* | (2006.01) |
| *A61P 17/02* | (2006.01) |
| *A61L 27/54* | (2006.01) |
| *A61L 27/60* | (2006.01) |
| *A61K 31/216* | (2006.01) |
| *A61K 9/48* | (2006.01) |
| *A61K 9/06* | (2006.01) |
| *A61L 15/44* | (2006.01) |
| *A61L 17/00* | (2006.01) |

(52) U.S. Cl.
CPC ........ *A61K 31/7048* (2013.01); *A61K 36/185* (2013.01); *A61L 15/44* (2013.01); *A61L 17/005* (2013.01); *A61L 27/54* (2013.01); *A61L 27/60* (2013.01); *A61P 17/02* (2018.01); *A61K 9/06* (2013.01); *A61K 9/48* (2013.01); *A61K 31/216* (2013.01); *A61K 2300/00* (2013.01); *A61L 2300/216* (2013.01)

(58) Field of Classification Search
CPC .............. A61K 31/7048; A61K 36/185; A61K 31/216; A61K 36/18–9068; A61P 17/02
See application file for complete search history.

(56) References Cited

U.S. PATENT DOCUMENTS

| | | |
|---|---|---|
| 5,897,880 A | 4/1999 | Drizen et al. |
| 5,981,606 A | 11/1999 | Martin |
| 6,800,286 B1 | 10/2004 | Olwin et al. |
| 8,410,055 B2 | 4/2013 | Li et al. |
| 2006/0018862 A1* | 1/2006 | Chen ................. A61K 8/0208 424/70.14 |
| 2006/0073132 A1 | 4/2006 | Congote |

OTHER PUBLICATIONS

Ambiga, S. et al., Ancient Science of Life, "Evaluation of Wound Healing Activity of Flavonoids from Ipomoea Carnea Jacq.", 2007, vol. XXVI, No. 3, pp. 45-51 (Year: 2007).*

Chen, W.-C. et al., Planta Med, "Effect of Topical Application of Chlorogenic Acid on Excision Wound Healing in Rats", 2013, vol. 79, pp. 616-621 (Year: 2013).*

Bigoniya, P. et al., Int. J. Pharm. Sci. Rev. Res., "Potential Wound Healing Activity of Euphorbia Hirta Linn Total Flavonoid Fraction" , 2013, pp. 149-156 (Year: 2013).*

Honnegowda, T. M et al., Plast Aesthet Res., "Role of angiogenesis and angiogenic factors in acute and chronic wound healing", 2015, vol. 2, pp. 243-249 (Year: 2015).*

Kim, H. H. et al., Arch. Pharm. Res., "Flavonoid constituents in the leaves of Myrica rubra sieb. et zucc. with anti-inflammatory activity", 2013, vol. 36, pp. 1533-1540 (Year: 2013).*

Nguyen, T. L. et al., Journal of Ethnopharmacology, "Flavonoids, gallotannins and ellagitannins in Syzygium guineense and the traditional use among Malian healers", 2016, vol. 192, pp. 450-458 (Year: 2016).*

Diaz-Gonzalez, M. et al., Biocatalysis and Biotransformation, 2012, vol. 30, No. 1, pp. 102-110 (Year: 2012).*

Nabavi, S. M. et al., Pharmacologyonline, "Determination of Antioxidant Activity, Phenol and Flavonoid Content of Parrotia Persica Mey", 2008, vol. 2, pp. 560-567 (Year: 2008).*

Tamri, P. et al., International Journal of Surgery, "Wound healing properties of quince seed mucilage: In vivo evaluation in rabbit full-thickness wound model", 2014, vol. 12, pp. 843-847 (Year: 2014).*

Trueb, Ralph; International Journal of Trichology, North American Virginian Witch Hazel (Hamamelis virginiana): Based Scalp Care and Protection for Sensitive Scalp, Red Scalp, and Scalp Burn-Out, 2014, vol. 6, No. 3, pp. 100-103 (Year: 2014).*

Basmadjian et al. "Cancer Wars: Natural Products Strike Back" *Frontiers in Chemistry*, 2, 2014, p. 20.

Burmistrova et al. "Antiproliferative Activity of Abietane Diterpenoids Against Human Tumor Cells" *Journal of Natural Products*, 76-8, 20 H, pp. 1413-1423.

Decicco-Skinner, et al. "Endothelial cell tube formation assay for the in vitro study of angiogenesis" *Journal of Visualized Experiments*, 91, 2014, pp. e51312-e51312.

Driver, et al. "The costs ot diabetic foot: the economic case for the limb salvage team" *Journal of vascular surgery*, 52(3), 2010, p. 17S-22S.

Hosseinzadeh et al. "Review of the Pharmacological and Toxicological Effects of *Salvia leriifolia*" *Iranian Journal of Basic Medical Sciences*, 12-1, 2009, pp. 1-8. (Abstract only).

(Continued)

*Primary Examiner* — Bahar Craigo
(74) *Attorney, Agent, or Firm* — Dority & Manning, P.A.

(57) ABSTRACT

Methods and compositions are described for use in encouraging angiogenesis and skin healing as may be utilized in wound treatment as well as in encouragement of angiogenesis in disease. Compositions include an effective amount of at least one of a flavonoid and a chlorogenic acid that are natural extracts of *Parrotia persica*, or their derivatives, analogues, or homologs. Compounds based upon these natural extracts have been found to be highly effective in vascular formation and skin closure while exhibiting low toxicity.

17 Claims, 7 Drawing Sheets

(56) References Cited

OTHER PUBLICATIONS

Hussein et al. "New adduct ot abietane-type diterpene from Salvia leriifolia Benth." *Nat Prod Res.*, 30(13), 2016. pp. 1511-1516. (Abstract only).
Kuhn, et al. "Balancing the pressure ulcer cost and quality equation" Nursing economic$, 10(5), 1991, pp. 353-359.
Merck & CO. "The Merck Index" 14$^{th}$ ed., Whitehouse Station, NJ, 2006.
Newman et al. "Natural Products as Sources of New Drugs Over the Last 25 Years" *Journal of Natural Products*, 70-3, 2007, pp. 461-477.
Sen, et al. "Human skin wounds: a major and snowballing threat to public health and the economy" *Wound Repair and Regeneration*, 17(6), 2009, pp. 763-771.
Siegel et al. "Cancer Statistics 2016" *CA: A Cancer Journal for Physicians*, 66-1, 2016, pp. 7-30.
Singer, et al. "Cutaneous wound healing" *New England Journal of Medicine*, 341(10), 1999, pp. 738-746.
Tecilazich, et al. "Emerging drugs for the treatment of diabetic ulcers" *Expert opinion on emerging drugs*, 18(2), 2013, pp. 207-217.
Wang, et al. "Enhanced keratinocyte proliferation and migration in co-culture with fibroblasts" *PloS One*, 7(7), 2012, p. e40951.
Wang et al. "Anti-Proliferative Effect of Jesridonin on Paclitaxel-Resistant EC109 Human Esophageal Carcinoma Cells" *International Journal of Molecular Medicine*, 2017, pp. 645-653.
Zhang et al. "Oridonin Effectively Reverses the Drug Resistance of Cisplatin Involving Induction of Cell Apoptosis and Inhibition of MMP Expression in Human Acute Myeloid Leukemia Cells" *Saudi Journal of Biological Sciences*, 24-3, 2017, pp. 678-686.

\* cited by examiner

COMPOUNDS FOR USE IN WOUND HEALING AND ANGIOGENESIS

CROSS REFERENCE TO RELATED APPLICATION

This application claims filing benefit of U.S. Provisional Patent Application Ser. No. 62/554,640 having a filing date of Sep. 6, 2017, and U.S. Provisional Patent Application Ser. No. 62/645,829 having a filing date of Mar. 21, 2018, both of which are incorporated herein by reference for all purposes.

FEDERAL RESEARCH STATEMENT

This invention was made with government support under grant no. 15510FC81 awarded by the National Science Foundation. The government has certain rights in the invention.

BACKGROUND

The successful treatment of wounds to regenerate healthy and functional skin remains a huge challenge due to the skin's multilayered structure, the presence of multiple different cell types organized within the extracellular matrix, and different biochemical pathways present in different wound types (e.g., acute wounds, chronic wounds, burns, etc.). An aging population and its requisite medical interventions, the continuing rise in diabetes and obesity, and an increase in the occurrence of traumatic wounds all translate to large increases in skin wounds needing treatment.

Particularly problematic are chronic non-healing wounds, which are estimated to affect approximately 2% of the general U.S. population. Patients with these hardest-to-heal wounds include those with diabetes, sickle cell ulcers, vasculitis, and scleroderma, as well as obese individuals. The cost of caring for chronic wounds in the U.S. alone is reported to exceed $50 billion annually.

While wound healing technology has grown rapidly, offering new products applicable for both acute (including both traumatic and surgical wounds) and chronic wound management, need for further improvement exists. For example, it is estimated that among the 2 million people diagnosed yearly with pressure ulcers, 900,000 remain non-healing after initial treatment, and reports indicate that of 800,000 diabetic foot ulcers treated in the U.S. yearly, 30% don't respond to common treatments.

Currently marketed drugs for use in severe wound treatment include Regranex® (Becarplermin), a genetically engineered recombinant platelet-derived growth factor, silver-based products such as silver sulfadiazine and Silvadene®, and wound dressings loaded with active ingredients such as silver, bismuth, chlorhexidine, bacitracin, hydrocortisone, or lidocaine. Growth factors such as transforming growth factor beta and fibroblast growth factors as well as Living Skin Equivalents (LSEs) are another class of advanced wound care products. Other products include different classes of keratolytics, antiseptics, sulfa-antibiotics, and collagen-specific enzymes. Many currently available wound healing medications are based on growth factors, cytokines, chemokines, collagen or hyaluronic acid. There are disadvantages associated with such agents due to side effects including inflammatory response and undesired stimulation of other cell types. There are also reported side effects for silver-containing products including bacterial resistance, cytotoxic effects, and hepatic or renal toxicity.

Such issues call for alternative wound healing agents that can provide more effective and rapid wound treatments with fewer side effects. Safer compounds that can promote the epithelialization and vascular formation in both acute and chronic wounds as well as other applications calling for similar activities would be of great benefit.

Natural products provide a historically successful source of medicinally active compounds and have the potential to provide targeted healing responses while limiting the undesirable side effects associated with many currently utilized treatments. Wound therapies based on natural compounds such as plant extracts and natural active components offer viable alternatives to synthetic pharmaceuticals, enhancing access to healthcare, and overcoming limitations associated with synthetic products and therapies, including high costs, long manufacturing times, and increased bacterial resistance.

SUMMARY

According to one embodiment, disclosed is a method for treatment of a wound. A method can include application of a composition to the wound, the composition including a flavonoid having the following structure (I):

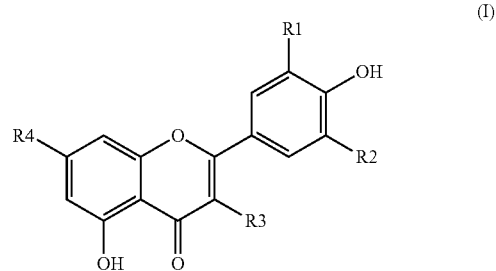

in which $R_1$, $R_2$, $R_3$, $R_4$, are independently selected from —H, —OH or a hexose. For instance, $R_1$, $R_2$, $R_3$, $R_4$, can be independently selected from —OH,

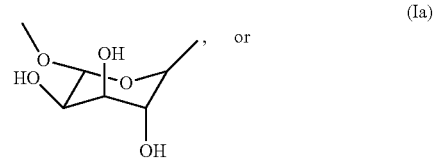

or

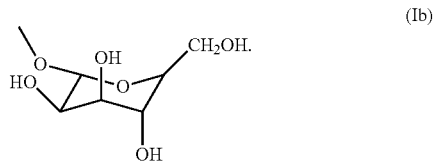

In one embodiment, a method can include application of a composition to the wound, the composition including a flavonoid of structure (I) in which $R_1$, $R_2$, and $R_4$ are —OH and $R_3$ is the structure (Ia), which is the structure of myrictin-3-o-rhamnoside as illustrated in FIG. 1.

In another embodiment, disclosed is a method for treatment of a wound. A method can include application of a composition to the wound, the composition including a chlorogenic acid having the following structure:

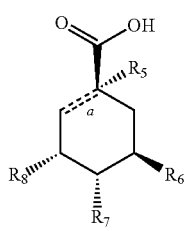

(II)

in which
a represents either a single bond or a double bond,
$R_5$ is present only when a represents a single bond,
$R_5$ (when present), $R_6$, $R_7$, and $R_8$ are independently either —OH or

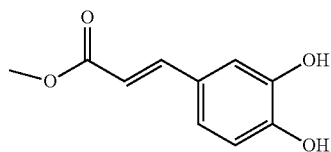

(IIa)

In one embodiment, a method can include application of a composition to the wound, the composition including a chlorogenic acid of structure (II) in which a is a single bond, $R_5$, $R_7$, $R_8$ are each —OH and $R_6$ is structure (IIa), which is the structure of 3-O-caffeoylquinic acid as illustrated in FIG. 2.

According to one method, a composition can include both a flavonoid of structure (I) and a chlorogenic acid of structure (II).

Beneficially, disclosed methods are applicable to different types of wounds including chronic wounds, acute wounds, and burns.

Also disclosed are methods for encouraging angiogenesis in an area. A method can include application of a composition to the area, the composition including a flavonoid of structure (I) and/or a chlorogenic acid of structure (II). Encouragement of angiogenesis may be useful in in treatment of diseases that do not necessarily encompass wound treatment.

Also disclosed are compositions that include at least one of a flavonoid of structure (I) and a chlorogenic acid of structure (II) in conjunction with a biocompatible carrier, e.g., at least one of myrictin-3-o-rhamnoside and 3-O-caffeoylquinic acid, in one embodiment. Disclosed compositions can include at least one of a flavonoid of structure (I) and a chlorogenic acid of structure (II) in conjunction with other active ingredients, which can vary depending, for example, on the type of wound for which the composition is intended or the particular disease being treated by use of the composition.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
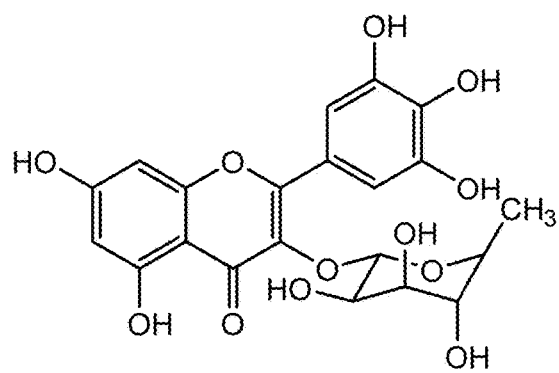
FIG. 1 presents the structure of myricetin-3-o-rhamnoside.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are methods and compositions for use in encouraging angiogenesis and skin healing as may be utilized in wound treatment as well as in treatment of disease in which increased angiogenesis is desirable. Disclosed are phenolic compounds based on natural extracts that can show efficacy in the prevention or treatment of disorders or pathologies of the skin, vascular disorders and/or problems linked to hyperseborrhea, or can be used as an anti-aging, healing, moisturizing, or pro-pigmenting agent.

Figure 2:
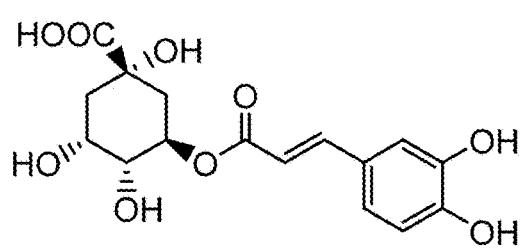
FIG. 2 presents the structure of 3-O-caffeoylquinic acid.

More specifically, compositions disclosed herein include an effective amount of at least one of a flavonoid and a chlorogenic acid that have been derived from natural extracts of *Parrotia persica*. The particular extracts upon which the disclosed compounds are based are myricetin-3-o-rhamnoside and 3-O-caffeoylquinic acid as depicted in FIG. 1 and FIG. 2, respectively. These natural extracts have been isolated from *P. persica* (commonly known as Persian ironwood), which is a deciduous tree in the family Hamamelidaceae, and is closely related to the witch-hazel genus *Hamamelis*. *P. persica* is native to northern Iran and southern Azerbaijan and is endemic in the Alborz mountains, and has traditionally been cultivated as an ornamental tree. Certain extracts of *P. persica* have been recognized for possible antibacterial and antifungal potential but the disclosed extracts and their analogs as disclosed herein have not previously been recognized as providing angiogenesis or other wound healing activity.

In one embodiment, a method or composition can incorporate a flavonoid having the following structure (I):

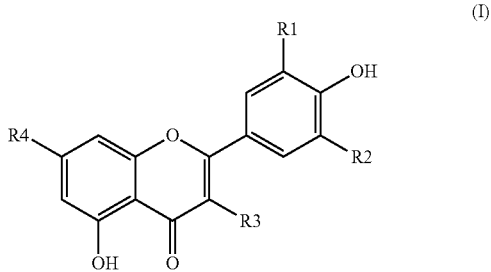

in which $R_1$, $R_2$, $R_3$, $R_4$, are independently selected from —H, —OH or a hexose. For instance, $R_1$, $R_2$, $R_3$, $R_4$, can be independently selected from —OH or

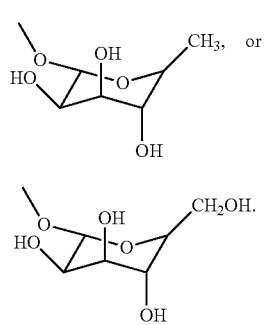

In one embodiment, disclosed is a flavonoid for application in wound healing or angiogenesis applications of structure (I) in which $R_1$, $R_2$, and $R_4$ are —OH and $R_3$ is the structure (Ia), which is the structure of myrictin-3-o-rhamnoside as illustrated in FIG.

Exemplary, non-limiting embodiments of flavonoids encompassed herein are those of structure (I) including R groups as shown in Table 1, below, and include a myricetin structure (I) in which all of $R_1$, $R_2$, $R_3$, and $R_4$ are —OH; myricetin-3-O-glucoside in which $R_1$, $R_2$, and $R_4$ are —OH and $R_3$ is a glucose; a quercetin in which $R_1$, $R_3$, and $R_4$ are —OH and $R_2$ is —H; quercetin-3-O-glucoside in which $R_1$ and $R_4$ are —OH, $R_2$ is —H and $R_3$ is a glucose; quercetin-3-O-rhamnoside wherein $R_1$ and $R_4$ are —OH, $R_2$ is —H, and $R_3$ is rhamnose; kaempferol in which $R_1$ and $R_2$ are —H and $R_3$ and $R_4$ are —OH; kaempferol-3-O-rhamnoside in which $R_1$ and $R_2$ are —H, $R_3$ is rhamnose, and $R_4$ is —OH; kaempferol-3-O-glucoside in which $R_1$ and $R_2$ are —H, $R_3$ is glucose and $R_4$ is —OH; and luteolin-7-O-glucoside in which $R_1$ is —OH, $R_2$ and $R_3$ are —H and $R_4$ is glucose.

TABLE 1

| Compound | $R_1$ | $R_2$ | $R_3$ | $R_4$ |
|---|---|---|---|---|
| Myricetin | OH | OH | OH | OH |
| Myricetin-3-O-rhamnoside | OH | OH | structure (Ia) | OH |
| Myricetin-3-O-glucoside | OH | OH | structure (Ib) | OH |
| Quercetin | OH | H | OH | OH |
| Quercetin-3-O-glucoside | OH | H | structure (Ib) | OH |
| Quercetin-3-O-rhamnoside | OH | H | structure (Ia) | OH |
| Kaempferol | H | H | OH | OH |
| Kaempferol-3-O-rhamnoside | H | H | structure (Ia) | OH |
| Kaempferol-3-O-glucoside | H | H | structure (Ib) | OH |
| Luteolin-7-O-glucoside | OH | H | H | structure (Ib) |

In one embodiment, a method or composition can incorporate a chlorogenic acid having the following structure (II):

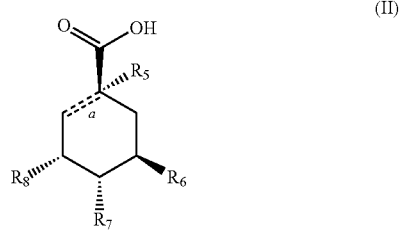

in which
a represents either a single bond or a double bond,
$R_5$ is present only when a represents a single bond,
$R_5$ (when present), $R_6$, $R_7$, and $R_8$ are independently either —OH or

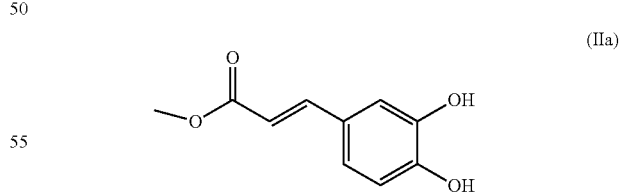

In one embodiment, disclosed is a chlorogenic acid for application in wound healing or angiogenesis applications of structure (II) in which a is a single bond, $R_5$, $R_7$, $R_8$ are each —OH and $R_6$ is structure (IIa), which is the structure of 3-O-caffeoylquinic acid as illustrated in FIG. 2.

Exemplary, non-limiting embodiments of chlorogenic acids encompassed herein are those of structure (II) including R groups as shown in Table 2, below, and include 4-caffeoylquinic acid, neochlorogenic acid (5-caffeoylquinic acid), dicaffeoylquinic acids wherein the 1 and 5 positions (1,5-dicaffeoylquinic acid), 1 and 3 positions (1,3-dicaffeoylquinic acid), 3 and 4 positions (3,4-dicaffeoylquinic acid), 3 and 5 positions (3,5-dicaffeoylquinic acid) are substituted, tricaffeoylquinic acid wherein 3, 4, and 5 position (3,4,5-tricaffeoylquinic acid) are substituted, and tetracaffeoylquinic acid wherein are 1, 3, 4 and 5 position (1,3,4,5-tetracaffeoylquinic acid), are substituted and caffeoylshikimic acids, and 5-O-caffeoylshikimic acid.

deposit collagen. Beneficially, disclosed compounds can encourage desirable activity at multiple stages of the wound healing process by various mechanisms including antimicrobial, anti-inflammatory, antioxidant, collagen synthesis stimulation, cell proliferative cell-stimulating and angiogenesis properties.

Compounds based upon the disclosed natural extracts can be effective in treatment of any type of wound in either external tissue (e.g., skin) or internal tissue (e.g., digestive

TABLE 2

| Compound | $R_1$ | $R_2$ | $R_3$ | $R_4$ |
|---|---|---|---|---|
| Quinic acid | OH | OH | OH | OH |
| 1-O-caffeoylquinic acid | structure (IIa) | OH | OH | OH |
| 3-O-caffeoylquinic acid | OH | structure (IIa) | OH | OH |
| Cryptochlorogenic acid (4-O-caffeoylqunic acid) | OH | OH | structure (IIa) | OH |
| Neochlorogenic acid (5-O-caffeoylquinic acid) | OH | OH | OH | structure (IIa) |
| 1,5-O-dicaffeoylquinic acid | structure (IIa) | OH | OH | structure (IIa) |
| 1,3-O-dicaffeoylquinic acid | structure (IIa) | structure (IIa) | OH | OH |
| 3,4-O-dicaffeoylquinic acid | OH | structure (IIa) | structure (IIa) | OH |
| 3,5-O-dicaffeoylquinic acid | OH | structure (IIa) | OH | structure (IIa) |
| 4,5-O-dicaffeoylquinic acid | OH | OH | structure (IIa) | structure (IIa) |
| 1,3,4,5-O-tetracaffeoylquinic acid | structure (IIa) | structure (IIa) | structure (IIa) | structure (IIa) |
| 3,4,5-O-tricaffeoylquinic acid | OH | structure (IIa) | structure (IIa) | structure (IIa) |

As described in more detail herein, compounds based upon these natural extracts have been found to be highly effective in vascular formation and skin closure while exhibiting low toxicity.

In vitro experiments using purified the myricetin-3-o-rhamnoside and 3-O-caffeoylquinic acid extracts, details of which are described further herein, have revealed a cell-specific and dose dependent response to both compounds for multiple types of skin and wound-related cells. In addition, the purified extracts and analogs as encompassed herein can demonstrate low toxicity. The combination of low toxicity with the ability to promote vascular formation and skin wound closure can be of great benefit, and disclosed compounds can be utilized in treatment of skin injuries in a variety of applications. For example, disclosed compounds can be used in combination with other known treatments in different stages of a wound healing process to enhance efficacy in various clinical applications.

Natural bioactive agents usually modulate multiple phases of the healing process, acting through a number of targets by inducing anti-inflammatory, antioxidant, and antibacterial effects. Similar to other natural bioactive agents, and unlike most modalities that only target one aspect of wound healing, disclosed compounds can simultaneously enhance multiple beneficial biochemical mechanisms. For instance, disclosed compounds can simultaneously promote the wound healing activities of keratinocytes and fibroblasts while also enhancing vascular tube formation.

Wound-healing encompasses multiple physiological processes including inflammation, cell proliferation, neovascularization, tissue granulation, re-epithelialization, and tissue reorganization. Re-epithelization involves migration and proliferation of epithelial tissue, primarily keratinocytes, and occurs in early wound repair. Angiogenesis is marked by endothelial cell migration and capillary formation responsible for delivering nutrients to the wound and helping maintain the granulation tissue bed. The final step of the proliferative phase is granulation tissue formation. Fibroblasts differentiate and produce ground substance as well as system, internal surgical sites). Non-limiting examples of wounds and skin injuries that can be treated by disclosed compositions include first, second, or third degree burn wounds resulting from exposure to heat, electricity, radiation (for example, sunburn or laser surgery), caustic chemicals, etc.; ulcers; hemorrhoids; wounds in diabetes mellitus; wounds, bedsores, and lesions caused by unrelieved pressure to any part of the body (especially portions over bony or cartilaginous areas); wounds due to external force damaging the tissue; skin wounds due to aging or the environment including splits, dry skin, roughness of the skin and the like; and ischemic syndromes such as coronary or peripheral arterial disease and angiogenesis-dependent disease. However, it should be understood that compositions based on one or both of these natural extracts have the potential to be effective against many other forms of wounds and skin disease outside of this small subset, and the use of this these compounds can be applied to the treatment of wounds, the prevention of scars, and the encouragement of angiogenesis in an array of diseases.

Compounds based on disclosed extracts can be provided in combination with other materials, including active agents and biocompatible carrier materials. Particular materials for use in conjunction with compounds based on one or both of the disclosed extracts can vary, depending upon the particular application of the composition. For instance, one or both of the disclosed compounds (or a derivative thereof, as described above) can be used alone or in combination with other products as a supplement or cosmetic. The compounds can be effective when formulated as skin conditioning, UV protective, or antiaging products in the form of a cream, a gel, an ointment, or a skin pad. More potent activities may be achievable for other applications of wound healing, for instance through semi-synthesis to augment its potential or in combination with other compounds.

A composition including one or more compounds derived from the disclosed extracts can be administered in any number of formats known to current pharmaceutical practice including, without limitation, solid wound dressings, gels, creams, ointments, liquid wound washers, etc. A composition may be stored for future use or may be formulated in effective amounts in conjunction with pharmaceutically acceptable carriers to prepare a wide variety of pharmaceutical compositions that can be stored or immediately used according to known practice. For instance, the compounds and/or compositions including the compounds can be protected from light and refrigerated to prolong the lifetime their use.

Disclosed compounds can be combined with any pharmaceutically acceptable carrier, adjuvant, or vehicle in formation of a composition. Examples of pharmaceutically acceptable carriers include, without limitation, pharmaceutical appliances, topical vehicles (non-oral and oral), ingestible vehicles and so forth. In addition, a pharmaceutical composition can be made using manufacturing techniques and processes readily known to those skilled in the art.

Compositions can be combined with pharmaceutical appliances for delivery to a wound or other area. Examples of pharmaceutical appliances include, without limitation, sutures, staples, gauze, bandages, burn dressings, artificial skins, liposome or micelle formulations, microcapsules, aqueous articles for soaking gauze dressings, and so forth.

In addition, ingestible compositions desirably can employ ingestible or partly ingestible vehicles such as confectionery bulking agents which include hard and soft vehicles such as, for example, tablets, suspensions, chewable candies or gums, lozenges and so forth.

Topical compositions may employ one or more carriers or vehicles such as, for example, creams, gels, foams, ointments, sprays, salves, bio-adhesives, films, fabrics and so forth, which are intended to be applied to the skin or a body cavity. Topical compositions may also be adapted for use as an oral vehicle such as, for example, mouthwashes, rinses, oral sprays, suspensions, and dental gels, which are intended to be taken by mouth but are not intended to be ingested. Topical ointments and other semi-solid compositions commonly employ one or more bases as a vehicle for drug delivery. Exemplary bases include, but are not limited to, hydrocarbon bases (e.g. white petrolatum, white ointment, vegetable oils, animals fats, etc.), absorption bases (e.g. hydrophilic petrolatum, anhydrous lanolin, lanolin, cold cream, etc.), water-removable bases (e.g. hydrophilic ointment USP, ethoxylated fatty alcohol ethers, ethoxylated lanolin derivatives, sorbitan fatty acid esters, etc.), and water-soluble bases (e.g. polyethylene glycol ointment, etc.).

A variety of traditional ingredients may optionally be included in the compositions in effective amounts. By way of non-limiting example, the compositions can contain one or more of the following materials: fillers, diluents, cleaning agents, buffers, preservatives, pH and toxicity modifiers, mechanical protectants, chemical protectants, adsorbents, antioxidants, viscosity modifiers, extenders, excipients, astringents, emollients, demulcents, humectants, emulsifiers, transdermal delivery enhancing agents, controlled-release agents, dyes or colorants, stabilizers, lubricants and so forth. These and other additives known to those having ordinary skill in the arts can be used in a composition as dictated by the nature of the delivery vehicle.

The amounts of additional components within the compositions are readily determined by those skilled in the art without the need for undue experimentation and will vary with the nature of the vehicle (e.g. a gel versus a spray), the wound to be treated, frequency of treatment and so forth. Thus, the amount of wound healing composition may be varied in order to obtain the result desired in the final product and such variations are within the capabilities of those skilled in the art without the need for undue experimentation. In a particular embodiment, a composition can comprise one or more compounds of the disclosed extracts present in an amount of about 50 wt. % or less and in a further embodiment in an amount of about 20 wt. % or less by weight of the composition. In a further embodiment, a compositions can contain one or more of the compounds in an amount between about 0.00001% to about 5%, by weight of the composition. In an alternate embodiment, a composition can include one or more of the compounds in an amount between about 0.001% to about 1%, by weight of the composition.

The clinical application and dosage of compounds based upon these extracts can be tailored to the skin condition or disease, patient size, medical history, method of delivery, etc.

Disclosed compounds can synergize with other known compounds for a single application or can be initially applied to an area so as to initiate migration and tube formation prior to the application of a second active agent, e.g., another known wound healing compound.

As described below, use of disclosed extracts can simultaneously provide an accelerated rate of wound healing in major physiological components of the wound healing process, which demonstrates the effectiveness of the compounds as wound healing agent. Results show reduced time of wound closure of keratinocyte and fibroblast using myricetion-3-o-rhamnoside and 3-O-caffeoylquinic acid compared to the control (growth media) after multiple different time intervals.

The present disclosure may be better understood with reference to the Examples set forth below.

EXAMPLE

Cell Culture and Reagents

Human Umbilical Vein Endothelial cells (HUVEC), Adult Normal Human Epidermal Keratinocytes (NHEK), Normal Human Dermal fibroblast (NHDF) and related media for cell culture including endothelial basal and growth medium-2 (EBM-2, EGM-2), keratinocyte basal and growth medium-2 (KBM-2, KGM™-2), fibroblast basal and growth medium (FBM, FGM™) were purchased from Lonza. The cell types were selected due to their important physiologic role in early and late stages of wound healing. Cells were incubated at 37° C. and 5% $CO_2$ throughout the examples. Phosphate-Buffered Saline (PBS), [3-(4,5-dimethylthiazol-2-yl)-5-(3-carboxymethoxyphenyl)-2-(4-sulfophenyl)-2H-tetrazolium (MTS) (Promega) colorimetric assay and growth factor reduced matrigel BD (Corning) were from Sigma-Aldrich.

Cytotoxicity Assay (MTS)

In order to determine cell viability, HUVECs, NHDFs, and NHEKs were cultured in their growth media to reach 80% confluency. Cells were seeded at the density of $5 \times 10^3$ cell per 96 well plate in a total volume of 100 µl in each well. After seeding, the cells were incubated for 24 hours at 37° C. and 5% $CO_2$ to allow for cell attachment. Media was changed and replaced with media supplemented with the desired concentration of the test compounds (10, 20, 50 and 100 µg/ml), being first dissolved at 10 mg/ml in DMSO and subsequently diluted in culture media. The vehicle control was culture medium supplemented with DMSO 0.5% (Macron Fine Chemicals), representing the highest final concentration of DMSO used to dissolve the natural compound. Following 24 hours of incubation, media containing 20% MTS solution was replaced with growth media and incubated for 2 hours. Colored formazan absorbance which was produced by bio-reduction of MTS tetrazolium compound in live cells was read at 490 nm using a Spectramax 190 spectrophotometer and cell proliferation was assessed. A standard calibration curve at different concentration of cells was prepared to correlate cell number to absorbance.

In Vitro Scratch Assay

Cell migration was assessed through making a scratch on confluent monolayers of NHDFs and NHEKs. A total of $15 \times 10^4$ cells per well were seeded on a 24 well plate and left overnight to reach confluency. The cell layer was then scraped using a 200 µl pipet tip and any cell debris was washed away with PBS. The samples were supplemented with different concentration of the compounds of interest in growth media and incubated at 37° C. and 5% $CO_2$ for 20 hours. Images were taken every 4 hours using a phase contrast Nikon Eclipse Ti-E inverted microscope. Quantification of percent wound healing was performed by measuring the gap distance using the following formula, $$\text{Wound closure \%} = \frac{(W_0 - W_n)}{W_0} * 100\%$$

where $W_n$ is the width of gap after every 4 hours and $W_0$ is the initial width zero right after forming a scratch.

Capillary Tube Formation

Matrigel kept in a −20° C. freezer and thawed on ice overnight in a 4° C. refrigerator. A total of 50 µl of thawed matrigel was added to each well of pre-chilled 96-well plate and then incubated for 30 min at 37° C. to form a gel. Next, 100 µl of a HUVEC cell suspension (passage 2-6) in conditioned media (20000 cell/well) including the compounds of this invention was added to gel and incubated at 37° C. for 8 hours. The number of junctions in tubes was examined using a phase contrast inverted microscope (Invitrogen EVOS FL Auto Cell Imaging) and compared to the conditions with no compound (negative control).

Experimental Results

Figure 3:
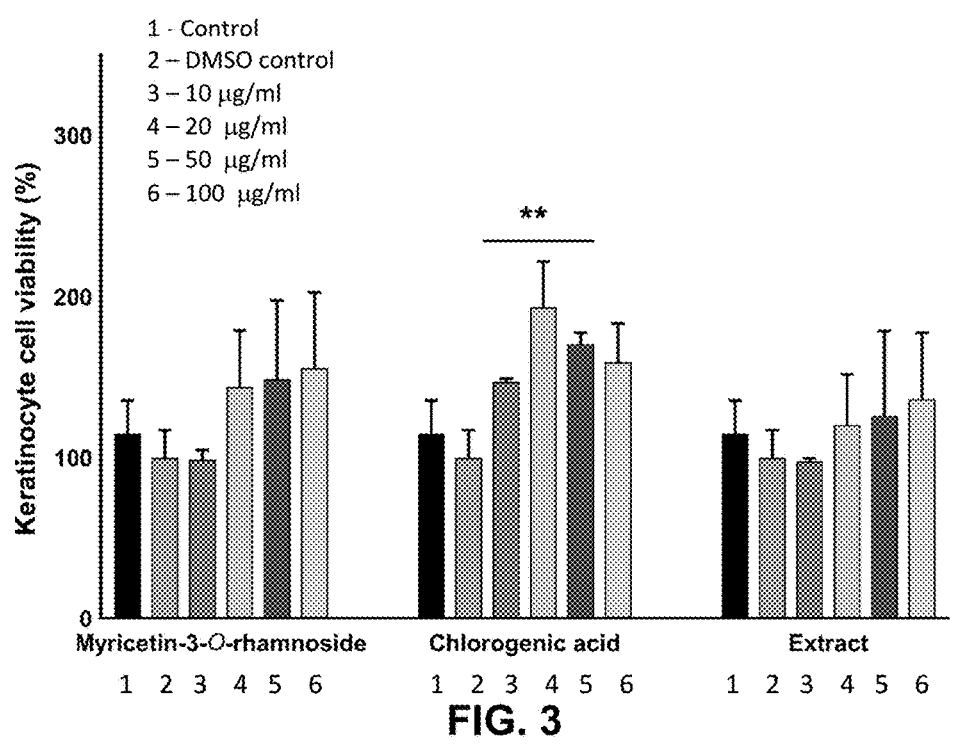
FIG. 3 graphically presents the effect of various concentrations of myricetin-3-o-ß-rhamnoside, 3-O-caffeoylquinic acid (as chlorogenic acid compound), and total extract of *P. persica* on cell proliferation for Normal Human Epidermal Keratinocytes (NHEKs).
Figure 4:
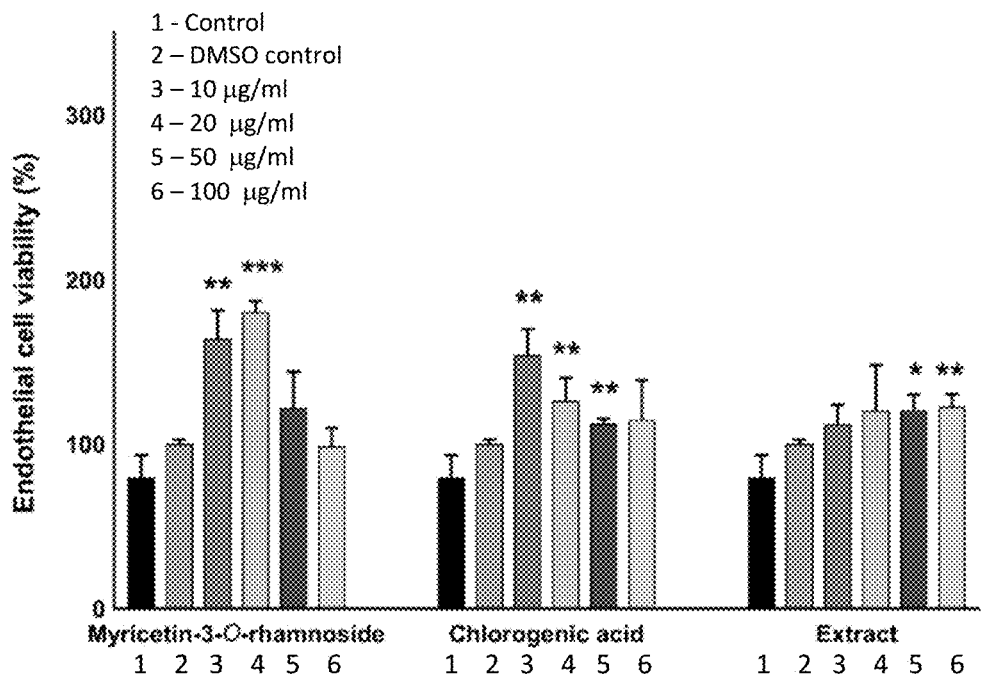
FIG. 4 graphically presents the effect of various concentrations of myricetin-3-o-ß-rhamnoside, 3-O-caffeoylquinic acid (as chlorogenic acid compound), and total extract of *P. persica* on cell proliferation for Human Umbilical Vein Endothelial Cells (HUVECs).
Figure 5:
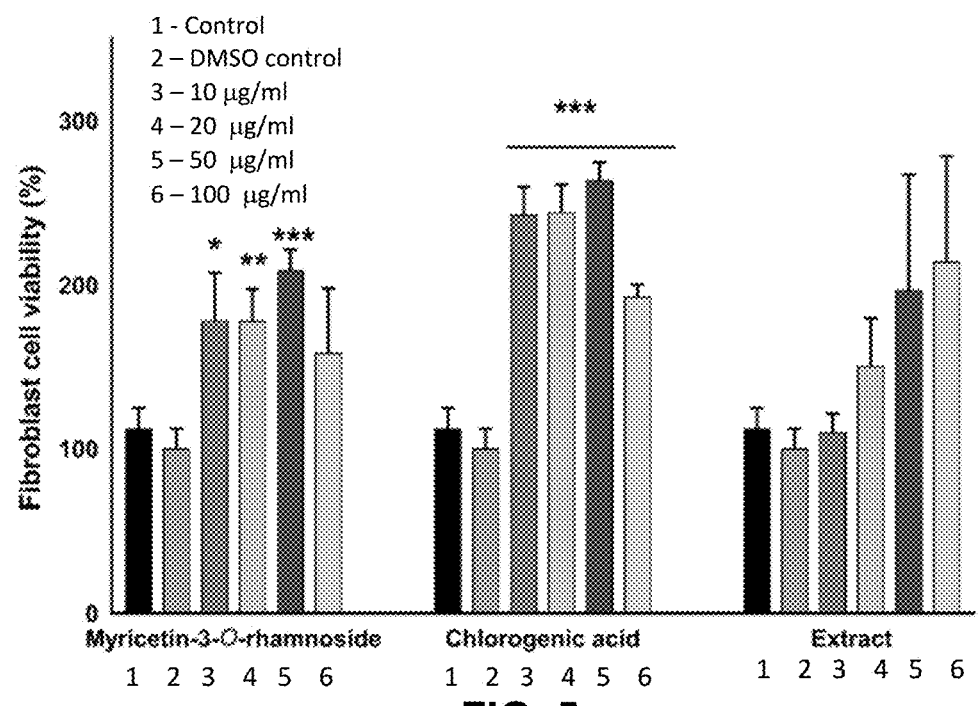
FIG. 5 graphically presents the effect of various concentrations of myricetin-3-o-ß-rhamnoside, 3-O-caffeoylquinic acid (as chlorogenic acid compound), and total extract of *P. persica* on cell proliferation for Normal Human Dermal Fibroblasts (NHDFs).

Cell proliferation and viability results were analyzed at 24 hours post seeding to find the optimum concentrations of the compounds and extract for angiogenesis and wound closure based on cytotoxicity analysis. FIG. 3, FIG. 4, and FIG. 5 present the effect of myricetin-3-o-ß-rhamnoside, 3-O-caffeoylquinic acid, and total extract of P. persica on cell proliferation of NHEKs (FIG. 3), HUVECs (FIG. 4), and NHDFs (FIG. 5). Cell viability (%) was calculated using an MTS assay after 24 h of exposure to the concentrations of the studied compounds as shown. No toxicity was observed in all three cell lines as compared to the control (untreated cells in growth media) and vehicle control (untreated cells in growth media containing control DMSO). Multiple t-tests were performed using Graph-Pad Prism 7.03 to determine the significance between each experimental group and the control (*p≤0.05, p≤0.01, and *p≤0.001).

Figure 6:
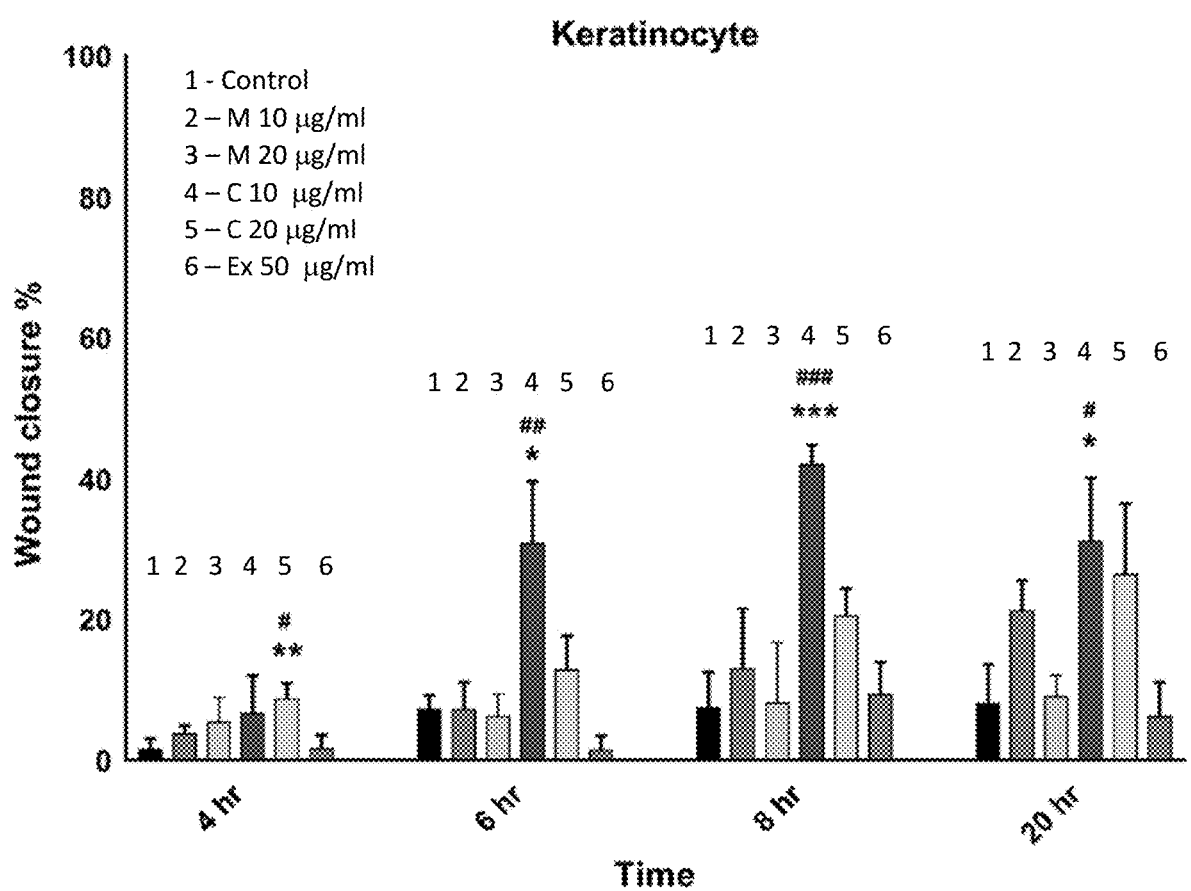
FIG. 6 graphically presents the simulated wound closure percentage of NHEKs after different time intervals of exposure to different concentrations of myricetin-3-o-ß-rhamnoside (M), 3-O-caffeoylquinic acid (C), and total extract of *P. persica* (Ex), as measured using a scratch assay.
Figure 7:
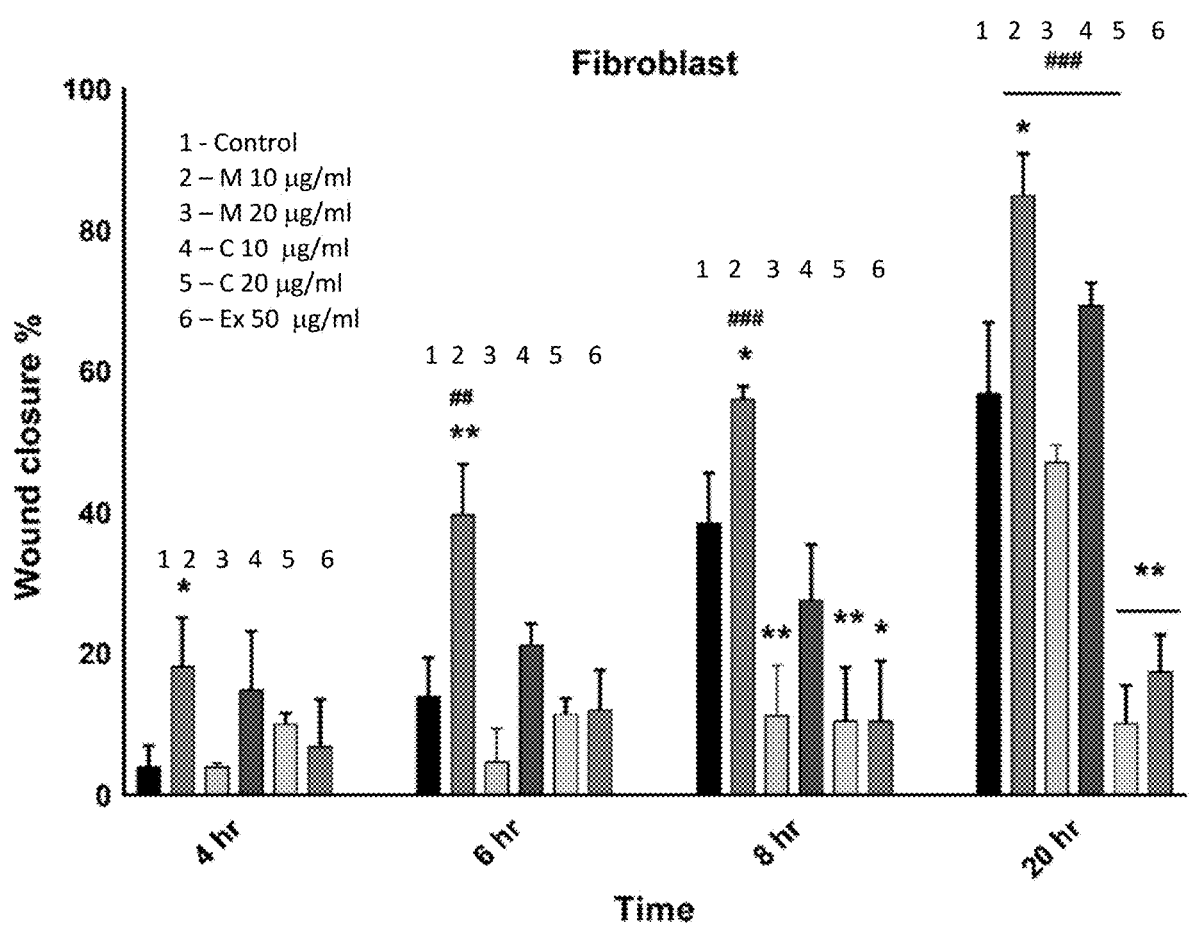
FIG. 7 graphically presents the simulated wound closure percentage of NHDFs after different time intervals of exposure to different concentrations of myricetin-3-o-ß-rhamnoside (M), 3-O-caffeoylquinic acid (C), and total extract of *P. persica* (Ex), as measured using a scratch assay.

FIG. 6 and FIG. 7 show the percentage of simulated wound closure over a time period of 20 h, at different time points of an assay, with two test concentrations (10 and 20 µg/ml). Controls were carried out using growth media, and growth media containing P. persica extract at a concentration of 50 µg/ml. The results demonstrated that NHEKs were most sensitive to 3-O-caffeoylquinic acid, showing the highest level of wound closure (FIG. 6). As early as 6 h, it was observed that approximately 40% of the gap had been closed with 10 µg/ml of 3-O-caffeoylquinic acid. A higher concentration of 3-O-caffeoylquinic acid, however, did not lead to a faster migration rate. Neither myricetin-3-o-ß-rhamnoside nor total P. persica extract led to a significantly higher NHEK gap closure than the control (FIG. 6). The analysis of wound closure using NHDFs demonstrated a contrasting pattern as compared to NHEKs (FIG. 7). Myricetin-3-o-ß-rhamnoside at a concentration of 10 µg/ml accelerated gap closure at all time points. The higher concentration of myricetin-3-o-ß-rhamnoside, however, had a negative effect on wound closure during early time points.

Figure 8:
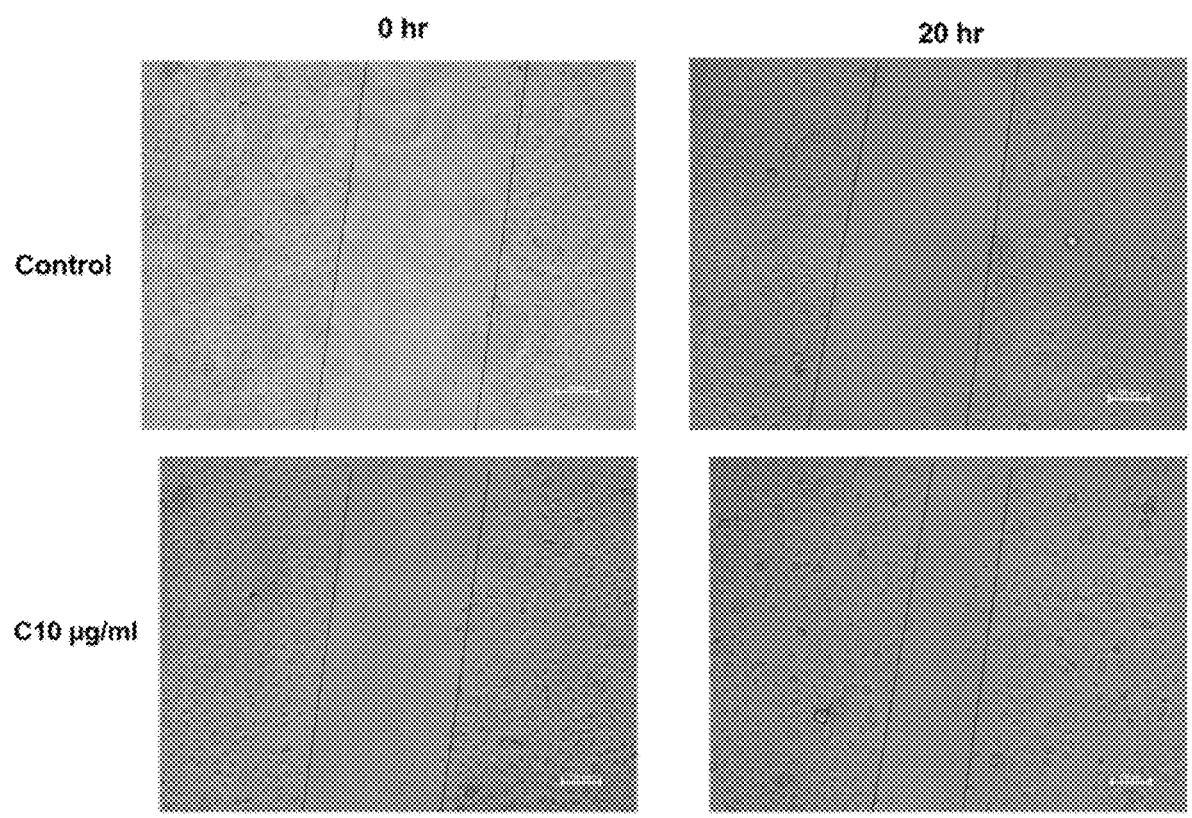
FIG. 8 illustrates the migration of keratinocytes toward a gap for a control system (top) and a system treated with 3-O-caffeoylquinic acid at 10 µg/ml (bottom).
Figure 9:
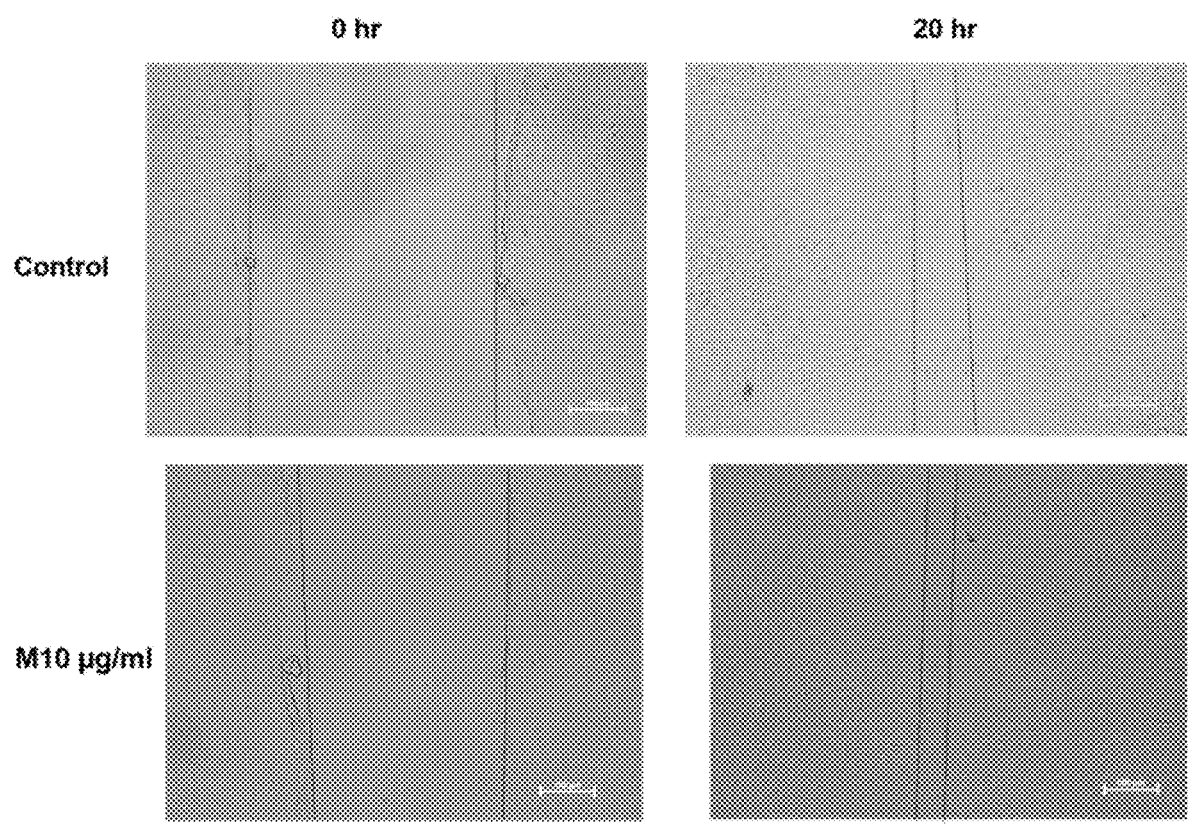
FIG. 9 illustrates the migration of fibroblast toward a gap for a control system (top) and a system treated with myricetin-3-o-rhamnoside at 10 µg/ml (bottom).

3-O-caffeoylquinic acid exhibited a delayed effect on NHDF gap closure at 20 h post-seeding. Similar to NHEKs, the extract did not accelerate the migration of NHDFs into the scratched gap as compared to the control. These results suggest a complementary effect of the two compounds in the wound healing models. This trend was valid until 20 hours after the treatment when the cells had nearly completed closing the wound. Multiple t-tests were performed using Graph-Pad Prism 7.03 to determine the significance between each experimental group and the control (*p≤0.05, p≤0.01, and *p≤0.001). Next, t-tests were performed to compare each pure compound group to the extract group (#p≤0.05, ##p≤0.01, and ###p≤0.001). The time progression of wound healing was demonstrated in a series of images taken from NHEKs and NHDSs migrating to fill the scratch under treatment with 3-O-caffeoylquinic acid (FIG. 8) or myricetin-3-O-rhamnoside (FIG. 9).

Figure 10:
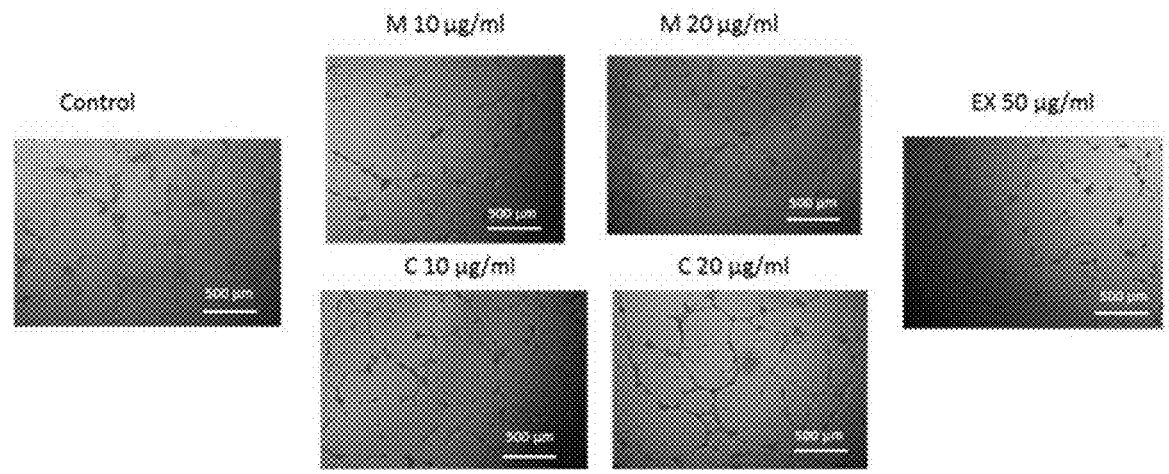
FIG. 10 presents phase contrast microscopy images of the vascular network during in vitro capillary tube formation of HUVECs treated in the absence or presence of myricetin-3-o-ß-rhamnoside (M), 3-O-caffeoylquinic acid (C), or the total extract (EX) of *P. persica* at various concentrations.
Figure 11:
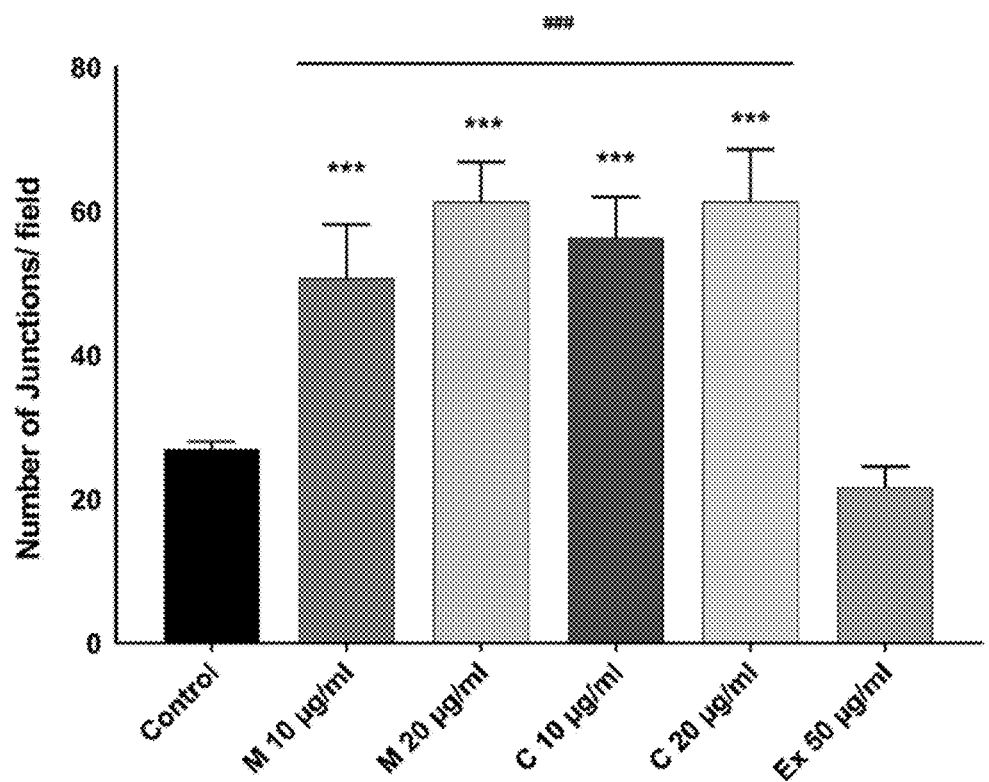
FIG. 11 graphically presents the number of junctions after 8 h of treatment of HUVECs treated in the absence or presence of myricetin-3-o-ß-rhamnoside (M), 3-O-caffeoylquinic acid (C), or the total extract (Ex) of *P. persica* at various concentrations.

In vitro capillary tube formation of HUVECs treated in the absence or presence of myricetin-3-O-ß-rhamnoside (M), 3-O-caffeoylquinic acid (C), or the total extract (EX) of P. persica was examined. The treatment of HUVECs on matrigel was examined with 10 and 20 µg/ml dose of the compounds. By use of phase contrast microscopy of the vascular network, marked changes were observed in the cell patterns, with the formation of tubules assembled by the elongation and joining of HUVECs in the presence of both myricetin-3-O-ß-rhamnoside and 3-O-caffeoylquinic acid (FIG. 10). Quantitative analysis of the data showed that the effect was clearly visible at 8 h when the number of junctions was approximately 3-fold higher than in the control groups (FIG. 11). Multiple t-tests were performed using Graph-Pad Prism 7.03 to determine the significance between each experimental group and the control (***p≤0.001). Next, t-tests were performed to compare each pure compound group to the extract group (###p≤0.001). The results indicate a pro-angiogenic activity of the pure compounds.

These results altogether delineate the potential to synergistically accelerate the fibroblastic and remodeling phases of wound repair by administering appropriate amounts of myricetin-3-O-ß-rhamnoside and 3-O-caffeoylquinic acid. Wound closure analysis was independent of mechanism.

While certain embodiments of the disclosed subject matter have been described using specific terms, such description is for illustrative purposes only, and it is to be understood that changes and variations may be made without departing from the spirit or scope of the subject matter.

What is claimed is:

1. A method for treatment of a wound, the method comprising contacting the wound with a composition, the composition comprising a total extract of *Parrotia persica*.

2. The method of claim 1, wherein the wound comprises an acute wound, a chronic wound, or a burn.

3. The method of claim 1, wherein the composition is applied during one or more additional wound phases.

4. The method of claim 1, wherein the composition is carried by a pharmaceutical appliance.

5. The method of claim 4, the pharmaceutical appliance comprising a suture, a stable, gauze, a bandage, a solid wound dressing, or an artificial skin.

6. The method of claim 1, the composition being in the form of a gel, a cream, or an ointment.

7. The method of claim 1, wherein the composition is contained within a capsule.

8. The method of claim 1, the composition further comprising one or more of quinic acid, 1-O-caffeoylquinic acid, 4-O-caffeoylqunic acid, 5-O-caffeoylquinic acid, 1,5-O-dicaffeoylquinic acid, 1,3-O-dicaffeoylquinic acid, 3,4-O-dicaffeoylquinic acid, 3,5-O-dicaffeoylquinic acid, 4,5-O-dicaffeoylquinic acid, and 3,4,5-O-tetracaffeoylquinic acid, 3,4,5-O-tricaffeoylquinic acid.

9. The method of claim 1, the composition further comprising one or more of myricetin, myricetin-3-O-glucoside, quercetin, quercetin-3-O-glucoside, quercetin-3-O-rhamnoside, kaempferol, kaempferol-3-O-rhamnoside, kaempferol-3-O-glucoside, and luteolin-7-O-glucoside.

10. The method of claim 1, the total extract of *Parrotia persica* comprising myricetin-3-O-rhamnoside and 3-O-caffeoylquinic acid.

11. The method of claim 10, the composition comprising the myricetin-3-O-rhamnoside in an amount of from about 0.00001% to about 5% by weight of the composition.

12. The method of claim 10, the composition comprising the 3-O-caffeoylquinic acid in an amount of from about 0.00001% to about 5% by weight of the composition.

13. The method of claim 1, the composition comprising the total extract of *Parrotia persica* in an amount of from 10 μg/ml to 100 μg/ml.

14. The method of claim 1, the wound comprising Adult Normal Human Epidermal Keratinocytes or Normal Human Dermal Fibroblasts.

15. The method of claim 1, wherein the wound is a chronic wound.

16. The method of claim 1, wherein the wound is a bedsore.

17. The method of claim 1, wherein the wound is a wound to an internal tissue.

* * * * *